United States Patent [19]
Kirkland et al.

[11] Patent Number: 5,948,531
[45] Date of Patent: Sep. 7, 1999

[54] PROPYLENE-BRIDGED BIDENTATE SILANES

[75] Inventors: Joseph J Kirkland, Wilmington; John B. Adams, Jr., Hockessin, both of Del.

[73] Assignee: Hewlett-Packard Company, Palo Alto, Calif.

[21] Appl. No.: 08/879,945

[22] Filed: Jun. 20, 1997

[51] Int. Cl.$^6$ ....................................................... B32B 5/16
[52] U.S. Cl. .......................... 428/405; 428/406; 556/406; 556/465
[58] Field of Search ..................................... 428/405, 406; 556/406, 465

[56] References Cited

U.S. PATENT DOCUMENTS

| | | |
|---|---|---|
| 3,505,785 | 4/1970 | Kirkland . |
| 3,722,181 | 3/1973 | Kirkland et al. . |
| 3,782,075 | 1/1974 | Kirkland . |
| 3,795,313 | 3/1974 | Kirkland et al. . |
| 3,979,546 | 9/1976 | Lewis . |
| 4,010,042 | 3/1977 | Boyer . |
| 4,010,242 | 3/1977 | Iler et al. . |
| 4,131,542 | 12/1978 | Bergna et al. . |
| 4,504,549 | 3/1985 | Pines et al. . |
| 4,600,646 | 7/1986 | Stout . |
| 4,666,717 | 5/1987 | Smith et al. . |
| 4,699,717 | 10/1987 | Riesner et al. . |
| 4,746,572 | 5/1988 | Glaich et al. . |
| 4,874,518 | 10/1989 | Kirkland et al. . |
| 5,108,595 | 4/1992 | Kirkland et al. . |

FOREIGN PATENT DOCUMENTS 0 129 074   12/1984   European Pat. Off. .

OTHER PUBLICATIONS

Jones et al., Characterization and Evaluation of Cyanopropyl Polysiloxane Stationary Phases for Gas Chromatography, 1984, vol. 298, pp. 389–397, Journal of Chromatography.

Lork et al., Role of the Functional Group in n–Octyldimethylsilances in the Synthesis of $C_8$ Reversed:Phase Silica Packings for High Performance Liquid Chromatography, (1986), vol. 352, pp. 199–211, Journal of Chromatography.

Boksanvi et al., Reaction of n–Alkylkimethylsilanols and n–Oxaalkyldimethylsilanols with the Hydrated Surface of Silicon Dioxide—The Question of the Limiting Surface Concentration, (1976), vol. 6, pp 95–137, Advances in Colloid and Interface Science.

Sindorf et al., Solid–State NMR Studies of the Reactions of Silica Surfaces with Polyfunctional Chloromethylsilanes and Ethoxymethylsilanes, 1983, vol. 105, pp. 3767–3776, J. Am. Chem. Soc.

Welsch et al., Characterization of a New Dehydroxylated Reversed–Phase Material, 1983, vol. 267 pp. 39–48, Journal of Chromatography 1985, vol. 103, p. 668, 71494v, Chemical Abstracts.

R.K. Iler "The Chemistry of Silica," pp. 97–98, John Wiley, NY, NY (1979).

Kirkland et al., Synthesis and Characterization of Highly Stable Bonded Phases for High–Performance Liquid Chromatography Column Packings, 1988, vol. 61, pp. 2–11, J. Am. Chem. Soc.

Kirkland et al., Stability of Silica–Based, Endcapped Columns with pH 7 and 11 Mobile Phases for Reversed–Phase High–Performance Liquid Chromatography, 1997, vol. A762, pp. 97–112, Journal of Chromatography.

Kirkland et al., High pH Mobile Phase Effects on Silica–Based Reversed–Phase High–Performance Liquid Chromatographic Columns, 1995, vol. A691, pp. 3–19, Journal of Chromatograhy.

Claessens et al., Effect of Buffers on Silica–Based Column Stability in Reversed–Phase High–Performance Liquid Chromatography, 1996, vol. A728, pp. 259–270, Journal of Chromatography.

Smith et al., The Efficient Analysis of Neutral and Highly Polar Pharmaceutical Compounds Using Reversed–Phase and Ion–Exchange Electrochromatography, 1995, pp. 197–203, Chromatographia vol. 41, No. 3/4.

L. R. Snyder and J.J. Kirkland, "An Introduction to Modern Liquid Chromatograph," Chapter 7, John Wiley, NY, NY (1979).

J. J. Kirkland et al., Bidentate Silane Statonary Phases for Reversed–Phase High–Performance Liquid Chromotography, Analytical Chem., vol. 70, No. 20, pp. 4344–4352, Oct. 15, 1998.

*Primary Examiner*—Robert Dawson
*Assistant Examiner*—Caixia Lu-Rutt
*Attorney, Agent, or Firm*—Mark Z. Dudley

[57] ABSTRACT

The present invention provides propylene-bridged bidentate silane reagents for modifying the surface of liquid chromatography supports, these supports and methods of making and using the same. When bonded to the surface of a support material, the resulting modified support material provides improved properties, such as better separations and more stable support materials, especially when used in liquid chromatography. These bidentate silanes have the general structure: $RSiMe(NMe_2)$—$(CH_2)_3$—$SiMeR$—$NMe_2$. R is an n-octadecyl group or an n-tetradecyl group, and Me is a methyl group. When reacted with a silica surface, the resulting modified surface has a structure: PSiO—[RSiMe—$(CH_2)_3$—SiMeR]—OSiP. PSiO is surface-reacted silica.

6 Claims, 6 Drawing Sheets

PROPYLENE-BRIDGED BIDENTATE SILANES

BACKGROUND OF THE INVENTION

1. Field of the Invention

The present invention relates generally to propylene-bridged bidentate silane reagents for modifying the surface of liquid chromatography supports, these supports and methods of making and using the same.

2. Discussion of Related Art

Liquid chromatography is an analytical method used to separate one or more species, such as ions or solutes, present in a carrier phase (i.e., solution) from the remaining species in the carrier phase. The carrier phase is typically passed through an open column packed with a granular material, commonly referred to as the support material. The most common support materials are silica-based.

The rate at which a particular solute passes through a chromatographic column depends upon the affinity of the solute for the support material, with solutes having a higher affinity for the support material passing through the column at slower rates. In certain cases, the affinity of a particular solute for the support material may be so high that essentially none of it passes through the column, resulting in substantially complete separation of that solute from the remaining species present within the carrier phase.

In large part, the affinity a solute has for a support material depends upon the functional groups present at the surface of the particles of the support material. Therefore, in many circumstances, it is desirable to bond modifying reagents containing certain functional groups to the surface of these particles to manipulate the rate at which different species pass through the column. For example, to separate an anionic species present in a carrier phase from a cationic species present in the carrier phase, a modifying reagent having cationic functional groups may be bonded to the surface of the particles of support material.

In addition to the functional groups contained within a surface modifying reagent, the strength of the bond between the reagent and the surface of a support material (i.e., stability of the modifying reagent) should be considered when choosing the reagent. If the bond between the modifying reagent and the support material surface is not strong enough, the modifying reagent can be released from the substrate during a liquid chromatography experiment. This can contaminate the separation product and/or reduce the efficiency of separation. Moreover, the ability of the modified support material to be re-used can be limited. Generally, a surface modifying reagent that bonds to the surface of a support material through two reagent atoms is more stable than a similar surface modifying reagent that only bonds to the surface through one reagent atom.

Still another factor to be considered when selecting a surface modifying reagent is the molecular structure that the reagent exhibits after it is bound to the surface of the support material. For example, the inherent variation of certain chemical and physical properties of polymers can result in problems with predicting the affinity of a given species for support materials having polymeric surface modifying reagents bonded thereto. Moreover, polymeric surface modifying reagents can cause problems with mass transport of a carrier phase through a liquid chromatography column, decreasing the efficiency of separation.

Silanes are the most commonly used surface modifying reagents in liquid chromatography. For example, "An Introduction to Modern Liquid Chromatography," Chapter 7, John Wiley & Sons, New York, N.Y. 1979; J. Chromatogr. 352, 199 (1986); J. Chromatogr., 267, 39 (1983); and Advances in Colloid and Interface Science, 6, 95 (1976) each disclose various silicon-containing surface modifying reagents. However, these reagents bond to the surface of support materials through only one silicon atom, reducing the stability of these substrate-reagent bonds.

U.S. Pat. Nos. 3,722,181 and 3,795,313; EP Patent Application 129,074; J. Chromatogr. 298, 389 (1984); and Angew. Cheme. Int. Ed. Engl. 25, 236 (1986) each disclose polymeric silicon-containing surface modifying reagents, but, according to U.S. Pat. No. 4,746,572, discussed below, the use of these reagents has resulted in problems with mass transport of carrier phases through columns. In addition, these columns can demonstrate a lack of predictability with respect to the affinity of certain species for the support materials, according to U.S. Pat. No. 4,746,572.

U.S. Pat. No. 4,746,572 discloses bidentate silanes for use as surface modifying reagents in liquid chromatography. This reference emphasizes the use of ethylene-bridged bidentate silanes and oxygen-bridged bidentate silanes. However, Anal. Chem. 61, 2 (1989) discloses that these silanes did not undergo complete reaction with the surface, and, as demonstrated in examples disclosed below, support materials having ethylene-bridged bidentate silanes bound thereto demonstrate nonoptimal performance in liquid chromatography separations.

From the foregoing discussion, it is clear that, despite the extensive efforts made in the art to provide improved surface modifying reagents for use in liquid chromatography, there remains a need to provide such reagents that exhibit improved stability under experimental conditions and predictability with respect to affinity to species in carrier phases. It would be advantageous for such reagents to be readily synthesized and easily bound to the surface of support materials.

SUMMARY OF THE INVENTION

In its broadest aspects, the present invention relates to propylene-bridged bidentate silanes that can be bonded to the surface of support materials to provide modified support materials that provide improved separations and higher predictability.

In one illustrative embodiment, the present invention provides a support composition having a structure: PSiO—[RSiMe—$(CH_2)_3$—SiMeR]—OSiP. R is an n-octadecyl group or an n-tetradecyl group. Me is a methyl group, and PSiO represents surface-reacted silica.

In another illustrative embodiment, the present invention provides a bidentate silane having a structure: RSiMe$(NMe_2)$—$(CH_2)_3$—SiMeR$(NMe_2)$. Me is a methyl group, and R is an n-octadecyl group or an n-tetradecyl group.

In yet another illustrative embodiment, the present invention provides a method of making a support composition. The method comprises mixing silica with a bidentate silane having a structure to form the composition. The bidentate silane has a structure: RSiMe$(NMe_2)$—$(CH_2)_3$—SiMeR—$NMe_2$. R is an n-octadecyl group or an n-tetradecyl group, and Me is a methyl group. The reaction forms a support composition having a structure: PSiO—[RSiMe—$(CH_2)_3$—SiMeR]—OSiP. PSiO represents surface-reacted silica.

In a further illustrative embodiment, the present invention provides a method of making a bidentate silane. The method comprises: reacting a Grignard reagent (RMgX) with allyl-methyldichlorosilane to form an allyl methyl R-chlorosilane; reacting the allylmethyl R-chlorosilane with R-methylchlorosilane in the presence of a platinum catalyst to form a bidentate chlorosilane; and reacting the bidentate dichlorosilane with dimethylamine to form a bidentate silane. X is a halogen atom, and Me is a methyl group. R is an n-octadecyl group or an n-tetradecyl group. The bidentate chlorosilane has a structure: RsiMeCl—(CH$_2$)$_3$—SiMeR—Cl, and the bidentate silane has structure: RSiMe(NMe$_2$)—(CH$_2$)$_3$—SiMeR—NMe$_2$.

BRIEF DESCRIPTION OF THE DRAWINGS

These and other advantages of the present invention will be more clearly understood when taken in conjunction with following detailed description and figures, in which.

DETAILED DESCRIPTION OF THE INVENTION

The present invention relates to propylene-bridged bidentate silanes which can be used as surface modifying species for chromatography support materials. It has been found that the resulting surface modified support materials provide more efficient separations. The propylene-bridged bidentate silanes can be used as surface modifying species for support materials for a variety of chromatography solid phase supports. Liquid column chromatography, thin layer chromatography, affinity separations and the like can benefit from the use of the propylene-bridged bidentate silanes of the invention. It has been demonstrated that the propylene-bridged bidentate silanes also exhibit a reduced rate of dissolution during liquid chromatography procedures at intermediate and high pH.

In accordance with the present invention, propylene-bridged bidentate silane reagents are provided that have a molecular formula:

wherein Me is a methyl group, R is an n-octadecyl group or an n-tetradecyl group, and NMe$_2$ is a leaving group that is capable of being displaced by an OH group attached to silicon, i.e. silanol. The present inventors have found that, when the leaving group is a dimethyl amino group, rupture of the Si—N in the silane bond is facile.

When optimizing the ability of a bidentate silane surface modifying reagent to improve the performance of a support material formed from silica, the conventional wisdom is that the distance between the silicon atoms of the silane should be about the same as the distance between the surface atoms to which the respective silicon atoms are bound. U.S. Pat. No. 4,746,572 (Glajch, et al.) reports that the distance between hydroxyl groups at a silica surface to which a bidentate surface modifying reagent can bond is about 5 Å. Glajch, et al. report that the distance between silicon atoms in ethylene-bridged bidentate silanes is also about 5 Å, thus bidentate silane modifying reagents having an ethylene bridge should bond well to the surface. The inventors of the present invention have determined, through computer molecular modeling using HyperChem, Version 4.0, from HyperCube, Inc. (Waterloo, Ontario, Canada) that the distance between oxygen atoms (hydroxyl groups) at a silica surface is from about 4.5 Å to about 5 Å, the distance between silicon atoms in an ethylene-bridged bidentate silane is about 5.4 Å, and the distance between silicon atoms in a propylene-bridged bidentate silane is about 6.2 Å. Based upon this molecular modeling information, as well as the information in U.S. Pat. No. 4,746,572, the use of ethylene-bridged bidentate silanes as surface modifying reagents for silica surfaces would be expected to provide better bonding between surface modifying reagent and surface than in the case of the propylene-bridged silanes. It would not have been expected that the propylene-bridged silanes of the present invention would perform as well as the ethylene-bridged silanes on silica surfaces. That is, one skilled in the art would not expect that increasing the distance between the silicon atoms in a bidentate silane would improve the ability of the silane to function as a surface modifying species for a liquid chromatography support surface. Therefore, it is an unexpected result that, when used as such surface modifying species, the propylene-bridged bidentate silanes of the present invention exhibit improved properties relative to ethylene-bridged bidentate silanes.

Without wishing to be bound by any theories, it is believed that the propylene-bridged bidentate silanes of the invention are able to space the hydrocarbon groups of the silane so that they are more readily accessed by solutes, resulting in better separations. In contrast, ethylene-bridged bidentate silanes may not be capable of properly spacing hydrocarbon groups. Instead, the hydrocarbon groups of ethylene-bridged bidentate silanes can aggregate. This reduces the ability of the solute to interact with the hydrocarbon groups, resulting in relatively poor separations. This effect is believed to be enhanced for silanes having longer hydrocarbon groups (e.g., n-octadecyl groups and n-tetradecyl groups).

The propylene-bridged bidentate silanes of the present invention can be reacted with silanol groups (Si—OH) at the surface of a silica support (packing material) to provide a support composition or surface complex or derivatives (modified support surface) having a molecular formula:

wherein PSiO represents reacted silica (i.e., silica that has undergone reaction with a propylene-bridged bidentate silane). These support compositions can be used in a variety of liquid chromatography experiments including, for example, reversed-phase chromatography, ion-exchange chromatography, size-exclusion chromatography, ion-pair chromatography, affinity chromatography and hydrophobic-interaction chromatography.

The word "bond" herein denotes a chemical bond, such as a covalent bond. Thus, for example, the interaction between a silicon atom and an oxygen atom at a silica surface may result in a covalent bond between the silicon atom and the oxygen atom. In most embodiments, the silicon atoms are covalently bound to the oxygen atoms at the surface of the reacted silica.

While silica is the preferred support material, other materials appropriate for use in the present invention are known to those skilled in the art and are intended to be within the scope of the present invention. For example, in certain embodiments, a hydroxylated organic polymer or plastic can be used.

In certain embodiments, a silica substrate may have a relatively small number of silanol groups present at its surface. For such embodiments, it may be desirable to hydrolyze the surface of the support material to increase the number of hydroxyl groups present at the surface of the support material. Such hydrolysis methods are known to those skilled in the art and are intended to be within the scope of the present invention. For example, surface hydrolysis of silica may be accomplished by reacting the support material with water in the presence of HF or at least one basic activator selected from the group consisting of quaternary ammonium hydroxides, ammonium hydroxide and organic amines at a temperature of from about 25° C. to about 100° C. for a period of time sufficient to generate the desired surface concentration of silanol groups (Si—OH).

The concentration of silanol groups on a silica surface can be determined in several ways including infrared spectroscopy, solid-state magic angle spinning nuclear magnetic resonance, proton spin counting space NMR, and/or thermogravimetric analysis, the latter generally being preferred because of its simplicity and precision. It is noted in this connection that excessive rehydroxylation of a silica surface to greater than about 8 $\mu$mol/m$^2$ of silanol groups will result in silanol groups that are "buried" beneath the silica surface. These groups are detected by TGA, but generally are not available for chromatographic interactions or for reactions with silanizing agents to form bonded-phase packings.

It has been found that activators which promote rehydroxylation to the desired total concentration of silanol groups of from about 6 to about 16 $\mu$mol/m$^2$ are HF and basic activators selected from the group consisting of quaternary ammonium hydroxides, ammonium hydroxide and organic amines. Preferably, the basic activator is selected from the group consisting of tetra alkylammonium hydroxide, ammonium hydroxides, primary organic amines and secondary organic amines. The relative rate of dissolution of silica by a basic activator can be controlled by maintaining pH in the weakly-basic range. Most primary and secondary organic bases rapidly dissolve silica above a pH of about 10.5. The rate is much slower below this pH value. A basic activator that provides a buffered pH of about 10.5 in dilute solution has desirable properties, especially when hydroxylation is carried out in a temperature range of from about 25° C. to about 50° C. At these temperatures, the solubility and the rate of transfer of silica is much lower than at higher temperatures, such as 100° C. Preferably, a basic activator is added in an amount sufficient to generate a pH of from about 9 to about 10.5.

For basic activators, the overall rate of attack on the silica surface generally decreases from methyl to ethyl to propyl. For example, normal ethyl-, propyl-, and butylamine, secondary ethyl-propyl- and butylamine are effective activators. Monomethyl- and dimethyl- are dimethylamine can be utilized, if care is exercised. Steric effects appear to have a not a noticeable influence on the dissolution rate of the silica gel lattice as disclosed by J. Chromatogr., Volume 149, 199 (1978). Methyl amines can be less practical because of their strong tendency to attack silica. Thus, methyl amines are more difficult to control in generating the desired concentration of silanol groups. It has been found that the rate of attack of a base on silica is dependent on the strength (pK$_B$ value), concentration, and geometry of a selected basic activator.

Although tetraalkylammonium hydroxides show strong aggressiveness for dissolving silica, these compounds are preferred basic activators for rehydroxylation. This is the case even though tetramethylammonium, tetrapropylammonium and tetrabutylammonium hydroxide show equal or an even greater tendency than alkali hydroxides to attack the silica surface. Tetraalkylammonium hydroxides are effective activators because at a pH of from about 9 to about 10.5, very little of the free base remains in solution. It is believed that most of the base is absorbed as a monolayer on the silica surface, making the silica somewhat hydrophobic. Hydroxyl ions remaining in solute catalyze the breaking of siloxane groups, while the monolayer of activator on the silica surface retards dissolution and deposition of silica. Therefore, the process can be conveniently interrupted before the degree of hydroxylation passes beyond the desired range.

Ammonium hydroxide is also a preferred basic activator. Dilute ammonium hydroxide a pH 10 reacted with silica for 18 hours and 25° C. is a preferred method for rehydroxylating a silica surface to the desired concentration if silanol groups. Hydrolysis of a 440 m$^2$/g silica by this procedure changed the surface area by only about 25%, and the pore volume of the silica remained essentially unchanged.

Most preferably, the basic activator is at least one primary amine selected from the group consisting of ethylenediamine, n-propylamine and n-butylamine. These amines can generate a pH of from about 9 to about 10.5. A pH in this range accelerates rehydroxylation of the silica surface, without significant change in the surface area and pore diameter of the silica structure as can occur with strong organic bases such as quaternary ammonium hydroxides. When the latter are used as activators, their concentration should be low and the initial pH should be not exceed about 10. Secondary amines such as diethyl-, dipropyl-, and dibutylamine are also suitable activators but rehydroxylation reactions are generally slower. Tertiary amines are less preferred activators.

Alkali- or alkaline-earth hydroxides such as NaOH, KOH and Ca(OH)$_2$ are difficult to control in the rehydroxylation process. Use of these agents can result in significant undesirable changes in the pore structure and surface area of the starting silica. In addition, use of these agents results in an undesired contamination of the starting silica with the cation from the hydroxide. This contamination causes deleterious effects with the silica support in subsequent chromatographic uses.

Acidic solutions of ionic fluorides are also suitable activators. Suitable sources of HF are HF, NH$_4$F and other ionic fluorides not containing a metal or metalloid cation which could deleteriously contaminate the highly purified silica. These activators can be added to an aqueous solution containing thermally dehydroxylated microspheres according to the following procedure. The aqueous solution is adjusted to a pH of about two to about four with a mineral acid such as hydrofluoric, hydrochloric or sulfuric acid. A suitable source of free HF is added to the solution in a concentration that acts as a catalytic agent for the dissolution of the silica surface. The preferred concentration of HF is a function of the surface area of the silica. Preferably, silica microspheres are rehydroxylated in the presence of free HF in a concentration of from about 50 to about 200 to about 400 ppm is suitable to activate the rehydroxylation of a 300–400 $m^2$/g silica. It is believed that fluoride, introduced as HF or an ionic slat thereof at a pH from about 2 to about 4, reacts with a small amount of dissolved silica to from $SiF_6^{-2}$. The $SiF_6^{-2}$ remains in equilibrium with a low concentration of HF. The fluoride ion at low pH functions as an activator to increase the rate of silica hydroxylation.

In addition to having atoms capable of reacting with a propylene-bridged bidentate silane (e.g., oxygen atoms) located at its surface, a support material (substrate) should provide the shape, rigidity, porosity and other physical characteristics desired for a given application. Generally, a support material can be in the form of various shapes as spheres, irregular shaped articles, rods, plates, films sheets, fibers, massive irregularly shaped objects and the like. Moreover, a support material can be porous or nonporous. In embodiments in which a support material is porous, where the pores are larger than a propylene-bridged bidentate silane reacted with the support material, the interior surfaces of the pores can have the propylene-bridged bidentate silane bonded thereto. For such embodiments in which the pores are smaller than the silane, the silane typically bonds only to the outside surface of the support material. The choice of support material depends upon the ultimate application, and one skilled in the art will readily recognize which properties a support material should have for a give use.

The support composition of the present invention are generally useful whenever highly stable surface modification of a liquid chromatography support material is desirable, and the functional groups introduced by the propylene-bidentate silanes of the present invention can be used in many ways. In particularly advantageous embodiments, the modified support materials are used as a point of attachment for substances of biological or synthetic organic interest, such as, for example, peptides, proteins and oligonucleotides. In these embodiments, synthesis of a desired biopolymer can be achieved by repetitive addition of individual monomers to the bidentate silane bonded to the substrate. The final biopolymer typically comprises 5 to 50 monomer units and typically is cleaved from the silane before use. The success of these syntheses depends upon many factors, one of which is the chemical stability of the substrate-to-silane bond. Known support materials often exhibit relatively short lifetime, which can cause problems with the reproducibility of results, usually leading to frequent replacement of the support material. In contrast, the relatively long lifetimes of the modified support materials of the present invention can be especially effective as stable, efficient media in the synthesis of biological or synthetic organic substances. In some embodiments, the modified support materials of the present invention can be used in conjunction with automated peptide, protein, and nucleotide synthesizer instruments.

In alternate embodiments, the support materials of the present invention are useful in applications in which it is advantageous to have a stable bond between a surface modifying species and a support material, such as in polypeptide sequencing applications. In these embodiments, the polypeptide to be sequenced is typically adsorbed to a filter disk coated with a non-bonded material such as Polybrene®, a polymeric quaternary amine. The polypeptide is then subjected to repetitive chemical degradation. A major disadvantage of this approach has been that the yields of the repetitive process are poor, at least in part due to loss of the non-bonded coating. However, substitution of the highly stable, modified support materials of the present invention can overcome these difficulties.

Reaction of the propylene-bridged bidentate silane with a silica surface should occur under conditions where the amount of water in the reaction mixture is insufficient to react with enough bidentate silane to deliteriously effect the synthesis procedure (dry conditions). Preferably, the reaction is carried out using a solvent that does not chemically react with the reagents used during synthesis of the surface composition. Such inert solvents include, for example, toluene, xylene and cymene. In certain embodiments, the solvent may be heated.

The chemistry of silanes with various surfaces is well-studied. A general discussion of the reaction of silanes with the surface of siliceous chromatographic support materials is provided in "An Introduction to Modern Liquid Chromatography," L. R. Snyder and J. J. Kirkland, Chapter 7, John Wiley and Sons, NY, N.Y. (1979). Additional details on the reaction of silanes with porous silicas are disclosed in "Porous Silica," K. K. Unger, p. 108, Elsevier Scientific Publishing Co., NY, N.Y. (1979). A broad description of the reactions of silanes with a variety of materials is given in "Chemistry and Technology of Silicones," W. Noll, Academic Press, NY, N.Y. (1968).

The performance of a particular modified support material generally improves as the surface coverage of a propylene-bridged bidentate silane bonded to the surface of the support material increases. According to the present invention, subsequent to the reaction of a bidentate silane with the surface of a support structure, the surface of the support structure should be saturated.

As used herein, a "saturated" silica surface refers to a silica surface which, subsequent to a reaction with a propylene-bridged bidentate silane, has substantially no nitrogen atoms bonded thereto as demonstrated by elemental analysis of the resulting modified support material.

It has been found that, during reaction of a propylene-bridged bidentate silane having a dimethylamino group bonded to each silicon atom with a silica substrate, rupture of the silicon-nitrogen bonds readily occurs, allowing a high rate of reaction between the silane and the surface of the support structure. It has also been found that using these bidentate silanes results in comparatively high coverages of silane on the surface of the silica surface subsequent to reaction of the silane with the silica surface.

The orientation of propylene-bridged bidentate silane is bound to a silica surface can be characterized by $^{29}$Si and $^{13}$C cross-polarization magic-angle-spinning nuclear magnetic resonance spectroscopy (CP-MAS NMR) and diffuse reflectance infrared Fourier transform spectroscopy (DRIFT), as described in J. Chromatogr., 264, 197–213 (1983) and J. Chromatogr., 352, 275 (1986). The orientation and bonding characteristics of the various Si atoms has been assigned by $^{29}$Si CP-MAS NMR. DRIFT spectroscopy can be used to identify the presence or absence of silanols at the surface of these modified support materials. The disappearance of a sharp peak at 3700 $cm^{-1}$ and the appearance of peaks in the 2800–3000 $cm^{-1}$ region of the spectra indicate the loss of isolated silanols and the formation of C—H structure due to bonding by the alkyl ligand.

The following examples are illustrative of certain embodiments of the present invention and are not to be construed as

EXAMPLE 1

1,3-Bis-(octadecyl methyl dimethylaminosilyl) propane $[(CH_3)_2N-Si-(CH_3)-C_{18}H_{37})CH_2]_2CH_2$ was prepared as follows. Allylmethyldichlorosilane (0.69 moles, available from the Aldrich Chemical Co., Milwaukee, Wis., USA) was put into a reaction flask with 250 milliliters of tetrahydrofuran (THF). One molar octadecylmagnesium chloride (0.65 moles) in THF was added portionwise to the flask while the mixture was stirred and cooling to a temperature range of about −10° to +5°. The temperature of this mixture was allowed to increase to 24°. Hexane was added to the mixture, and the solid filtered off. The filtrate was evaporated on a rotary evaporator to leave an oil. The oil was vacuum-distilled, providing 134.7 g (55.8% relative to the theoretical yield) of ally methyl octadecyl-chlorosilane (compound A) as a clear, colorless oil. The boiling point of compound A was 188°/0.1–191°/0.2 mm, and gas chromatography/mass spectrometry (GC/MS) showed 100% compound A.

Octadecylmagnesium bromide was generated in the usual way by combining 36.5 g (1.5 moles) of magnesium turnings and 500 g (1.5 moles) of octadecyl bromide (from Acros Organics/Fisher Scientific Co., USA) in 1200 milliliters of THF. The Grignard solution was transferred to a dropping funnel under nitrogen pressure via double point syringe needle, and added over a 1.8-h period to a solution of 181.6 grams (1.6 moles) of methyldichlorosilane in 250 milliliters of THF while cooling this mixture to a temperature of 5 to 10°. After warming to 22° the mixture was diluted with hexane and filtered. The filtrate was evaporated to a clear, colorless oil on a rotary evaporator. Vacuum distillation of this oil yielded 108 g of octadecyl methyl chlorosilane (compound B) as a clear, colorless oil. This oil had a boiling point of 175–177°/0.5 mm. GC/MS showed 98.9% compound B and 0.8% of the bis-(octadecyl methylsilyl) ether.

Compound B (134.4 grams, (0.4 moles) and 2.8 mL of 0.05M solution of $H_2PtCl_6$ (platinum catalyst) in ethyl acetate were added to a reaction flask. This mixture was heated to a temperature range of 56° to 96° while 75 grams of compound A (of a total of 142 g to be added) was added portionwise to the mixture. After 16 hours at ambient temperature, the reaction mixture was heated at 90° while the remaining portion of compound A was added portionwise. This mixture was held at 100° for three hours, and a 47 gram portion of the resulting reaction solution was vacuum-distilled. This provided 29 g (62% of theoretical yield) of 1,3-bis-(octadecyl methyl chlorosilyl)propane (compound C) as a clear, amber oil with a boiling point of 293–297/(0.1–0.2 mm). Compound C partly solidified. Analysis calculated for compound C was $C_{41}H_{86}Cl_2Si_2$ (formula weight 706.21): C, 69.73; H, 12.27; Cl, 10.04%. Elemental analysis showed: C, 69.78; H, 12.41; Cl, 9.60%, demonstrating the high purity of the resulting compound.

Compound C (27.2 grams, 0.0385 moles) was added to a reaction flask fitted with a dry-ice condenser. Liquified dimethylamine (11 milliliters, 0.2 moles) was dripped into the flask over 40 minutes, producing a mixture thick with solid. Hexane (300 milliliters) were added to the flask, and this mixture was stirred and filtered. The filtrate was evaporated on a rotary evaporator to yield 25.5 g (91.4% of theoretical yield) of 1,3-bis-(octadecyl methyldimethylaminosilyl)-propane (compound D) as a clear, gold-colored oil. Analysis calculated for compound D, $C_{45}H_{96}N_2Si_2$ (formula weight 723.45): C, 74.71; H, 13.65; N, 3.87%; and elemental analysis found: C, 74.86; H, 13.85; N, 3.62%.

It is noted that 1,3-bis-(tetradecyl methyl dimethylaminosilyl)propane can be prepared by a method analogous to that described for compound D.

EXAMPLE 2

Silica (35 g, Zorbax Rx-SIL, 80 Å, 183 m²/g, available from Hewlett-Packard Co., Wilmington, Del.) and 250 milliliters of toluene were added to a 500-mL flask. The mixture was stirred and boiled under reflux, with azeotropic removal of water and 56 mL of toluene. The moisture trap was replaced with a dry reflux condenser, and the mixture was cooled below reflux. Compound D (32.6 grams) was added, and this mixture was stirred and boiled under reflux for 71 hours. The hot mixture was filtered, washed with hot: toluene; THF; and acetonitrile. A sample of the product was dried in a vacuum oven at 110° with an air sweep, at 20" Hg vacuum for 2 hours. Elemental analysis of the dried sample showed: C, 11.94; H, 2.07; N, 0.03%. This silica derivative was capped with dimethylsilyl and trimethylsilyl groups (J. Chromatogr. A97, 762 (1997)). Elemental analysis of this capped composition showed: C, 12.10; H, 2.07; N, 0.04%. The comparatively small amount of nitrogen indicated that the reaction between the bidentate silane surface of the support structure was substantially complete.

It is noted that the 1,3-bis-(tetradecyl methyldimethylamino-silyl)-propane reagent can be substituted for the compound D to produce the analogous composition.

EXAMPLE 3

Figure 1:
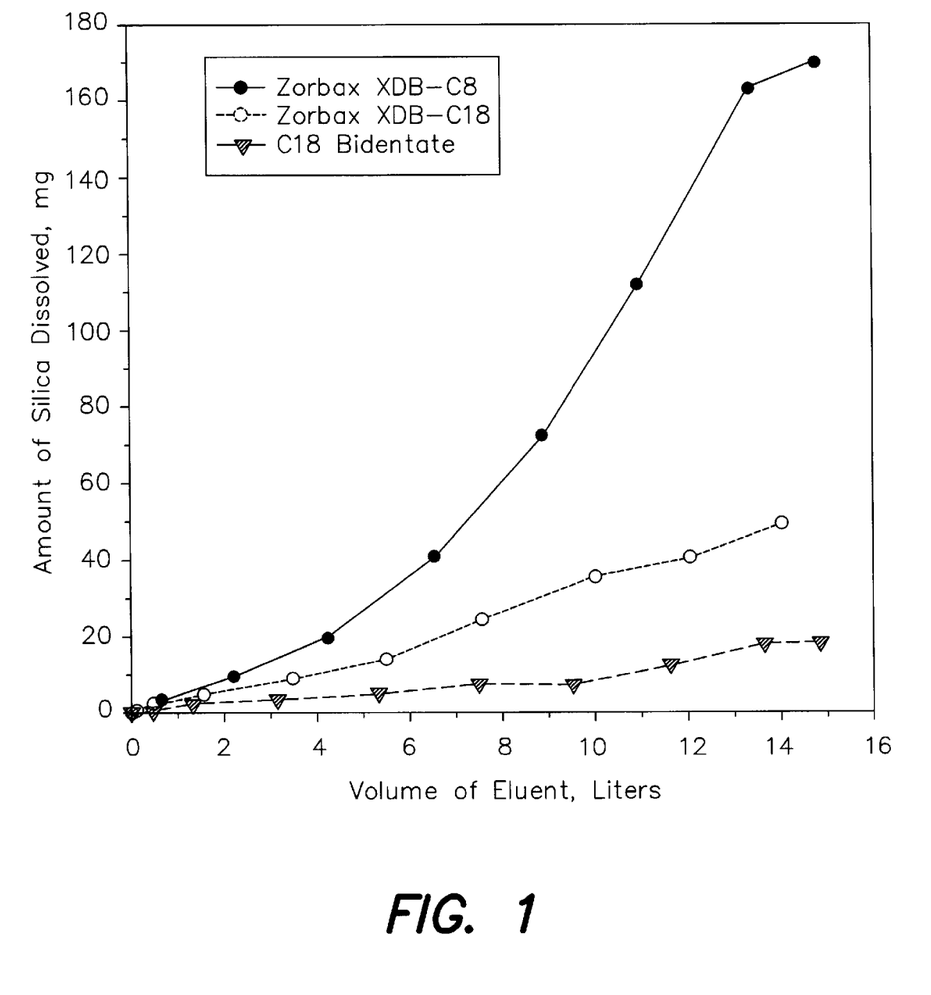
FIG. 1 is a graph comparing the dissolution of a modified support material according to one embodiment of the present invention with dissolution of modified support materials according to the related art.

FIG. 1 compares the stability at high carrier phase pH of modified support silica having $(CH_3)C_{18}H_{37}$—Si—$(CH_2)_3$—$Si(CH_3)C_{18}H_{37}$ propylene-bridged bidentate silanes bonded thereto with the stability of conventional $Si(CH_3)_2C_8H_{17}$ and $Si(CH_3)_2C_{18}H_{37}$ monofunctional (i.e., one silicon atom) silanes bonded to silica surfaces. The bonded silanes were double-endcapped with dimethylsilane and trimethylsilane groups (J. Chromatogr. A762, 97 (1997)).

These experiments were conducted in 15 cm×0.46 cm chromatographic columns which were continuously purged with mobile phase at 25°. The purge mobile phase for the dissolution studies was composed of 50% acetonitrile/50% 0.02M potassium phosphate buffer at a pH of 11.0. To duplicate actual chromatographic practice, columns were continuously purged at 1.5 mL/min with eluents and not recycled. This procedure is considered to be superior to simulated column aging studies in which packings are immersed in a static volume of mobile phase for a time period. In simulated column aging studies, the chromatographic process actually is not simulated, since the solution in contact with the mobile phase becomes saturated and the support does not further dissolve.

After beginning a specific dissolution experiment with continuous purging, the effluent was sampled after about one liter had passed through the column, using a fraction collector. Column effluent samples for silicate analysis were collected for a 6 min period (9 mL total).

Silicate concentrations dissolved from the columns were measured calorimetrically at 410 nm for collected fractions using the well-known silicomoybdate complex method, as described in "The Chemistry of Silica," R. K. Iller, p. 97 John Wiley, NY, N.Y. (1979).

For these silica measurements, standard silica mixtures were prepared in the corresponding buffer-modifier purge solutions used for the dissolution studies. Absorbance values were measured using blank solutions as reference. The potential interference of phosphate on the colorimetric method was eliminated by removing phosphate prior to silica measurement, as discussed in J. Chromatogr. A691, 3 (1995).

Results from the calorimetric measurements for the concentration of dissolved silica in the eluents were plotted as a function of effluent volume. The total silica dissolved from the column was first determined by using the silica average of two consecutive fractions. From this, the corresponding immediate eluent was calculated. By multiplying these values and summing the mass of silica over the total effluent volume, cumulative plots then were obtained that represented the mass of silica that had been dissolved as a function of eluent volume purged through the column.

As shown in FIG. 1, modified support materials having the bidentate $C_{18}$ silane of the present invention showed a strikingly lower silica support solubility rate, i.e. much better stability with a pH 11 phosphate-containing mobile phase than the conventional monofunctional dimethyl-C8 and dimethyl-C 18 stationary phases. Without wishing to be bound by any theories, it is believed that this is due to the bonding of the propylene-bridged bidentate silane via two silicon atoms, resulting in the hydrophobic bonded silanes forming a protective blanket that inhibits the silica support against attack by hydrophilic hydroxyl ions.

EXAMPLE 4

Figure 2:
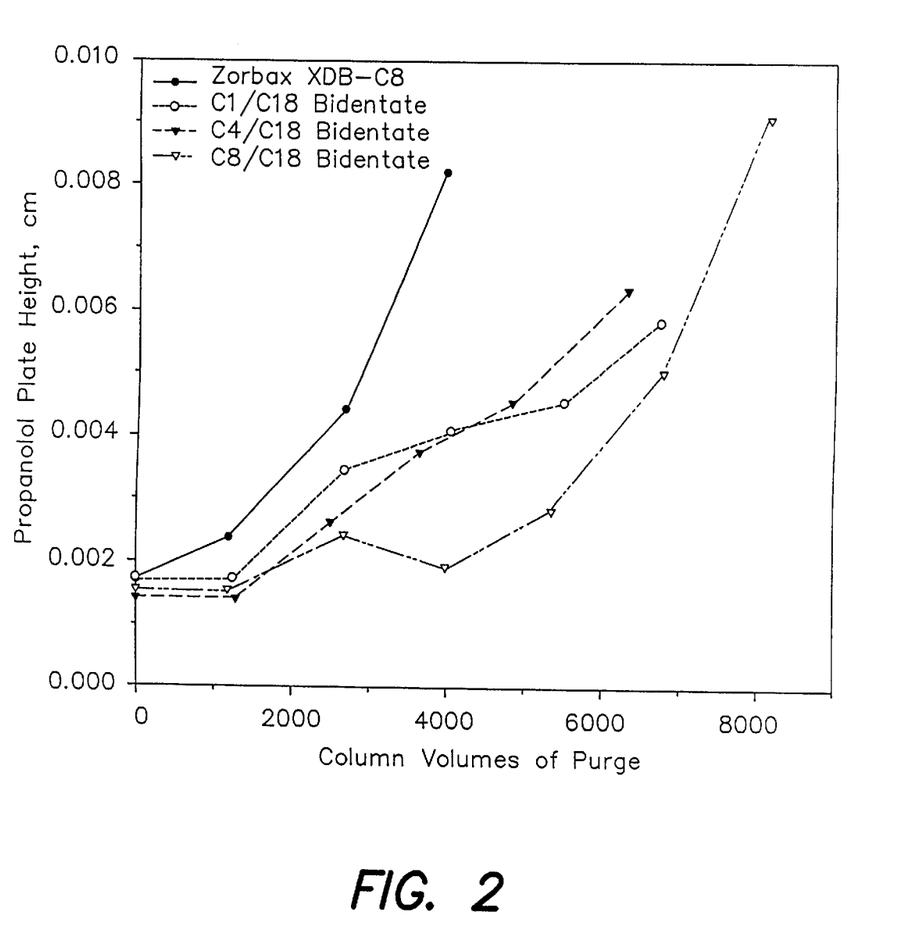
FIG. 2 is a graph comparing the basic drug propanolal plate height of a modified support material according to one embodiment of the present invention with that of modified support materials according to the related art.

FIG. 2 compares the stability of the silanes of Example 3 in chromatographic experiments. As shown in FIG. 2, the bidentate silane of the present invention is more stable than the conventional monofunctional silanes. In the experiments of FIG. 2, each column was continuously purged with a mobile phase consisting of 50% acetonitrile/50% 0.017M potassium phosphate buffer, pH 11.0 at 1.5 mL/min and ambient temperature (23°). The plate height of a basic solute, propanolol, was used as a measure of column degradation, with an increase in plate height signifying degradation of the column packing as a result of dissolution of the silica support under the high pH conditions.

EXAMPLE 5

Figure 3A:
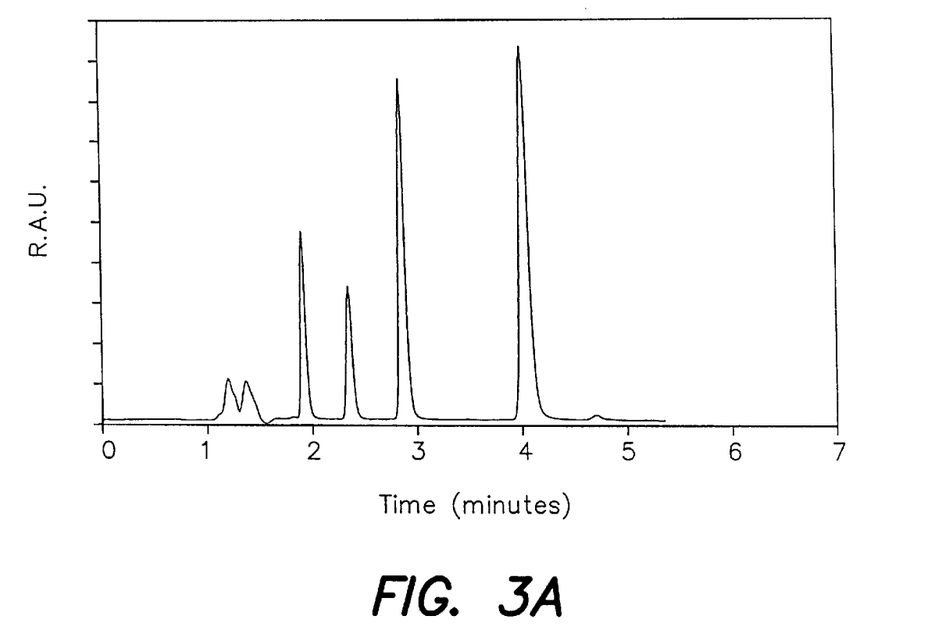
FIGS. 3A and 3B are graphs showing the separation by a chromatographic column having a modified support material according to one embodiment of the present invention before (FIG. 3A) and after (FIG. 3B) over 9,000 flushings with a high pH mobile phase.
Figure 3B:
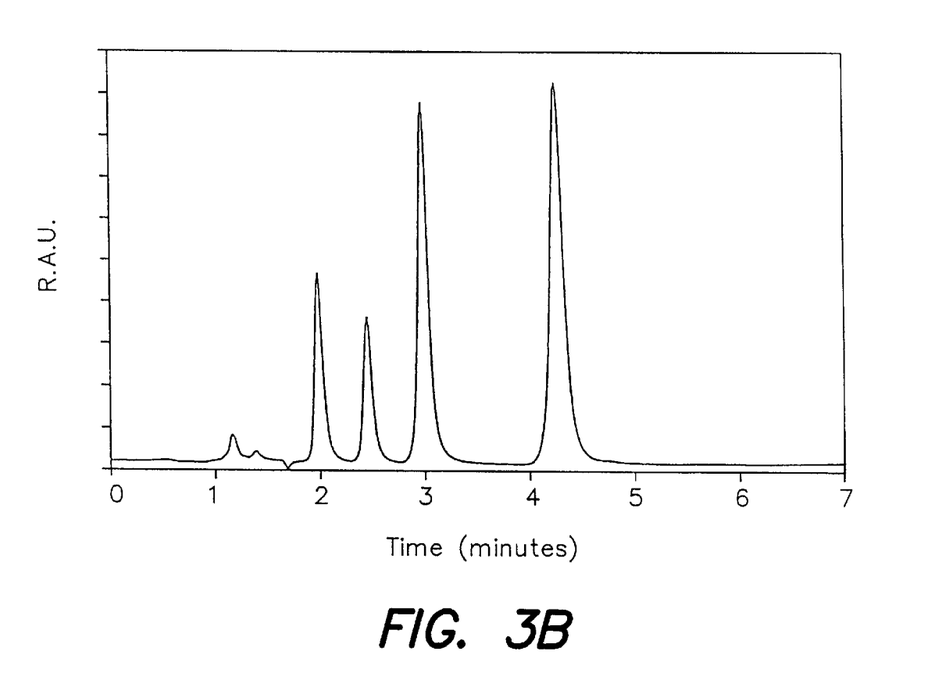

FIGS. 3A and 3B show the initial separation, in terms of relative absorption units (R.A.U.) as a function of retention time, by the modified support materials of Example 3, of a mixture of highly basic ($pK_a$=9.5–9.7) beta-blocker drugs (FIG. 3A) and the same mixture after the column had been purged after 9,419 column volumes of the aggressive phosphate-containing mobile phase of Example 2 (FIG. 3B). As shown in FIG. 3, the modified support material having the bidentate silane of the present invention shows only slight degradation.

EXAMPLE 6

Figure 4:
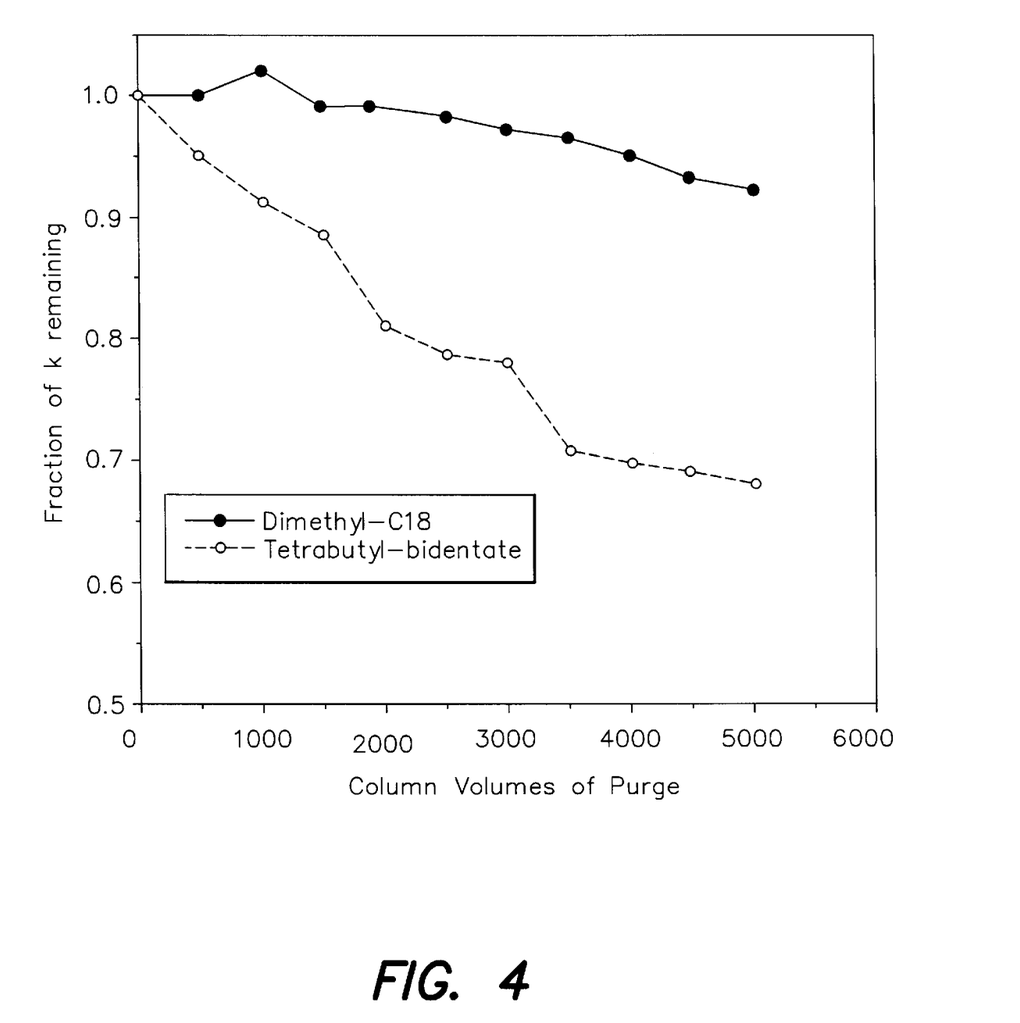
FIG. 4 shows the fraction of (k) remaining for chromatographic columns having modified support materials according to the related art.

FIG. 4 compares the stability, at low pH, of $(C_4H_9)_2$—Si—$(CH_2)_2$—Si$(C_4H_9)_2$ and Si$(CH_3)_2C_{18}H_{37}$ (both related art silanes). At low pH, silanes can be hydrolyzed from the silica support surface, resulting in a loss of organic stationary phase and a decrease in the retention of most solutes. As shown in FIG. 4, due to the greater bulk of the C18 groups, the modified support material having monofunctional dimethyl-C18 silane bonded thereto shows less degradation (is more stable) at about pH 2 and 50° than the modified support material having ethylene-bridged bidentate silane bonded thereto.

EXAMPLE 7

Figure 5:
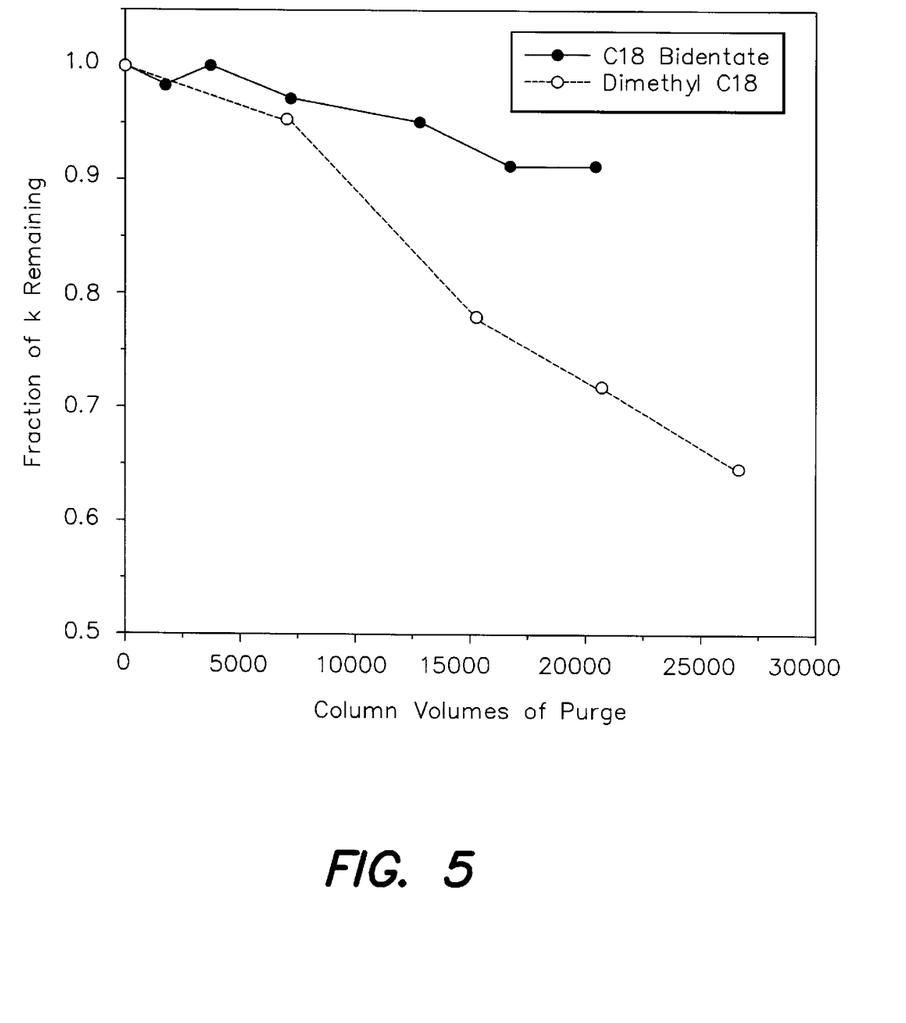
FIG. 5 shows the fraction of k remaining for a chromatographic column having a modified support material according to one embodiment of the present invention and a chromatographic column having a modified support material according the related art.

FIG. 5 compares the stability, at low pH, of $(CH_3)C_{18}H_{37}$—Si—$(CH_2)_3$—Si$(CH_3)C_{18}H_{37}$ (present invention) with Si$(CH_3)_2C_{18}H_{37}$. In contrast to the support material with ethylene-bridged silane, the modified support material having the propylene-bridged bidentate silane of the present invention is more stable than the modified support structure having the monofunctional dimethyl-C18 silane bonded thereto. The experiments of FIG. 5 were similar to those of FIG. 4 except that, in FIG. 5, the mobile phase was 1% trifluoroacetic acid (pH~0.9) and the temperature was 90°. It is to be noted that other propylene-bridged bidentate silanes, such as those with C14 groups, show similar advantages over conventional monofunctional dimethyl-C14 column packing materials.

EXAMPLE 8

Figure 6A:
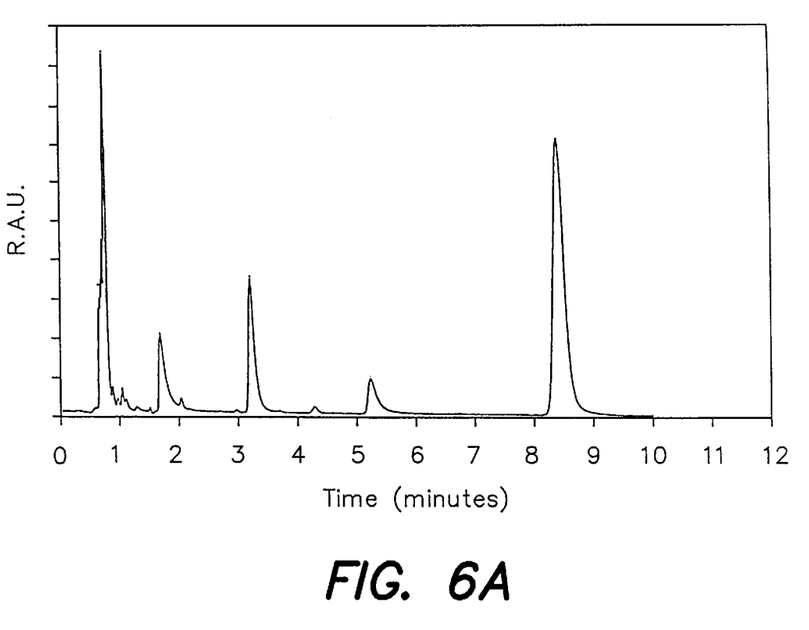
FIGS. 6A and 6B show separations achieved with a chromatographic column having a modified support material according to one embodiment of the present invention (FIG. 6B) and a chromatographic column having a modified support material according to the related art (FIG. 6A).
Figure 6B:
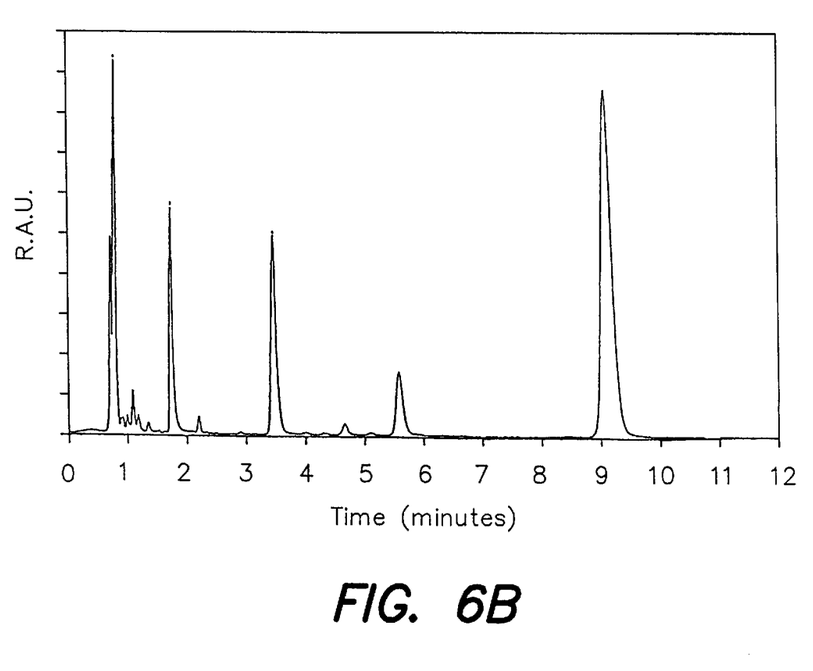

FIGS. 6A and 6B compare the separation, in terms of R.A.U. as a function of retention time, of a mixture of basic tricyclic antidepressant drugs for modified support materials having $(CH_3)C_{18}H_{37}$—Si—$(CH_2)_3$—Si$(CH_3)C_{18}H_{37}$ (present invention) bonded thereto and modified support materials having $(CH_3)C_{18}H_{37}$—Si—$(CH_2)_2$—Si$(CH_3)C_{18}H_{37}$ (prior art) bonded thereto. The propylene-bridged silane column of the present invention shows higher plate number and lower peak asymmetry values than the ethylene-bridged column, indicating superior kinetics (mass transfer). The propylene-bridged column also shows greater retention for these and other solutes.

Additional comparative results are shown in Table 1.

TABLE 1

| Phase | Reaction time, hrs. | % $C^a$ | Amitriptyline[b] | | |
|---|---|---|---|---|---|
| | | | N | k | As |
| Zorbax XDB-C8 | 24 | 7.15 | 9002 | 3.77 | 1.53 |
| Zorbax XDB-C18 | 72 | 9.38 | 9055 | 6.44 | 1.47 |
| C1/C18 bidentate | 18 | 9.08 | 8802 | 6.02 | 1.84 |
| C4/C18 bidentate | 21 | 9.13 | 9607 | 5.86 | 1.49 |
| C4/C18 bidentate | 72 | 9.32 | 9923 | 5.98 | 1.39 |
| C8/C18 bidentate | 18 | 10.50 | 10035 | 5.55 | 1.27 |
| C18/C18 bidentate | 71 | 12.09 | 5990 | 5.22 | 2.07 |
| C18/C18[c] bidentate | 72 | 12.09 | 4413 | 5.25 | 3.37 |
| C18/C18P bidentate | 71 | 11.94 | 9377 | 5.31 | 1.57 |

P= propylene bridge
[a]After double endcapping
[b]60% ACN/40% 0.01 M Na phosphate buffer, pH 7.0, 1.0 mL/min, 40° C.
[c]Reaction in p-cymene at 165° C.

In Table I, "N" represents the plate height of a column, "k" is a normalized retention value of a column, and "As" is the peak assymetry value in the corresponding chromatograph. These terms are known to those skilled in the art and are described in, for example, "An Introduction to Modern Liquid Chromatography," L. R. Snyder and J. J. Kirkland, Second Edition, John Wiley, NY, N.Y. (1979).

Having thus described certain embodiments of the present invention, various alterations, modifications and improvements will be apparent to those skilled in the art. Such alterations, modifications and improvements are intended to be within the spirit and scope of the present invention. Accordingly, the foregoing description is by way of example only and not to be construed as limiting. The present invention is limited only as described by the following claims and the equivalents thereto.

What is claimed is:

1. A support composition having a structure:

wherein R is an n-octadecyl group or an n-tetradecyl group, Me is a methyl group and PSiO is surface-reacted silica.

2. The support composition according to claim 1, wherein the support composition is endcapped.

3. The support composition according to claim 2, wherein R is an n-octadecyl group.

4. The support composition according to claim 2, wherein R is an n-tetradecyl group.

5. The support composition according to claim 1, wherein R is an n-octadecyl group.

6. The support composition according to claim 1, wherein R is an n-tetradecyl group.

* * * * *